United States Patent [19]

Taylor et al.

[11] 4,174,209

[45] Nov. 13, 1979

[54] HERBICIDAL 1-ALKYL-3-PHENYLPYRIDINIUM SALTS

[75] Inventors: Harold M. Taylor, Indianapolis; Robert G. Suhr, Greenfield, both of Ind.

[73] Assignee: Eli Lilly and Company, Indianapolis, Ind.

[21] Appl. No.: 917,038

[22] Filed: Jun. 19, 1978

[51] Int. Cl.² .................. C07D 213/26; C07D 213/28; A01N 9/22
[52] U.S. Cl. ........................................ 71/94; 546/290; 546/296; 546/297; 546/301; 546/302; 546/303; 424/263

[58] Field of Search .................. 260/294.8 R, 290 HL, 260/296 R, 297 R; 71/94; 546/290, 296, 297, 301, 302, 303

[56] References Cited

U.S. PATENT DOCUMENTS

| | | | |
|---|---|---|---|
| 3,260,723 | 7/1966 | L'italien et al. | 546/290 |
| 4,102,689 | 7/1978 | Taylor | 546/290 |
| 4,128,555 | 12/1978 | Butler | 546/290 |
| 4,152,136 | 5/1979 | Taylor | 71/90 |

*Primary Examiner*—Alan L. Rotman
*Attorney, Agent, or Firm*—Leroy Whitaker; Arthur R. Whale

[57] ABSTRACT

A class of 1-alkyl-3-phenylpyridinium salts are useful herbicides. The compounds bear a meta-substituent on the phenyl ring and optional 4- and 5-substituents.

32 Claims, No Drawings

HERBICIDAL 1-ALKYL-3-PHENYLPYRIDINIUM SALTS

BACKGROUND OF THE INVENTION

This invention belongs to the field of agricultural chemistry, and provides new herbicides, herbicidal methods and herbicidal compositions.

Since the discovery of 2,4-D in the 1940's, research in herbicides has been conducted at a high pitch and with excellent results in many fields. Herbicides are now in demand and in wide use for killing and controlling weeds growing in cropland, and also for the control of unwanted vegetation of all kinds, such as on fallow land and industrial property.

Paraquat, 1,1'-dimethyl-4,4'-bipyridinium ion, usually used as the dichloride, is an excellent quick-acting contact herbicide. It is chemically quite remote from the compounds of the present invention.

SUMMARY OF THE INVENTION

This invention provides new compounds of the formula

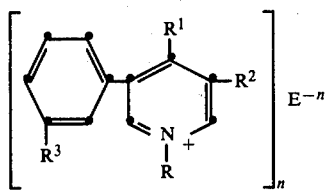

wherein R represents methyl or ethyl;

$R^1$ represents halo, methoxy, $C_1$–$C_4$ alkylthio, benzylthio or dimethylamino;

$R^2$ represents hydrogen, phenoxy, phenylthio, $C_1$–$C_4$ alkyl, $C_1$–$C_4$ alkoxy, $C_1$–$C_4$ alkylthio, phenyl or phenyl monosubstituted with chloro, bromo, fluoro, trifluoromethyl, $C_1$–$C_3$ alkyl or $C_1$–$C_3$ alkoxy;

$R^3$ represents $C_1$–$C_3$ alkyl, $C_1$–$C_3$ alkoxy, trifluoromethyl, chloro, fluoro or bromo;

E represents an anion capable of forming a pyridinium salt; and n represents an integer of 1 to 3.

The invention also provides a method of reducing the vigor of unwanted herbaceous plants which comprises contacting the plants with a herbicidally-effective amount of a compound described above, and herbicidal compositions which comprise an agriculturally-acceptable carrier and a compound described above.

DESCRIPTION OF THE PREFERRED EMBODIMENT

In the above formulae, the general chemical terms are used in their usual meanings in the organic chemical art. For example, the term halo refers to bromo, chloro, fluoro and iodo. The terms $C_1$–$C_4$ alkyl, $C_1$–$C_4$ alkoxy, $C_1$–$C_4$ alkylthio, $C_1$–$C_3$ alkyl and $C_1$–$C_3$ alkoxy refer to such groups as methyl, ethyl, isopropyl, butyl, t-butyl, methoxy, ethoxy, isopropoxy, t-butoxy, s-butoxy, methylthio, ethylthio, propylthio, isobutylthio and butylthio.

As organic chemists will understand, the anions used in the present compounds include any and all anions, having valences from 1 to 3, which are capable of forming pyridinium salts. Typical illustrative anions include such as chloride, bromide, iodide, fluoride, trifluoromethanesulfonate, methanesulfonate, fluorosulfonate, sulfate, hydrogen sulfate, phenylsulfonate, phenylsulfonate substituted with $C_1$–$C_3$ alkyl or alkoxy groups, particularly toluenesulfonate, nitrate, phosphate, hydrogen phosphate, monosodiumsulfonate, mono- or disodium phosphate, and the like. Thus, it will be understood that multivalent anions such as sulfate, phosphate and the like may have one or more cations associated with them, as for example protons or alkali metal cations. It will further be understood that, when the anion is multiply charged, as the sulfate anion for example, each anion will be associated with an appropriate number of pyridinium radicals. For example, in the case of the sulfate anion, two pyridinium radicals are associated with each sulfate anion.

Agricultural chemists will immediately understand that the addition of commonly-used substituents to the compounds of this invention may be expected to produce active compounds equivalent to those explicitly described herein. For example, such substituents as halogen atoms, $C_1$–$C_3$ alkoxy, alkylthio and alkyl groups, and trifluoromethyl groups, as well as functional groups such as hydroxy, alkoxycarbonyl and cyano groups, may be added to the compounds. In particular, phenoxy and phenylthio $R^2$ groups may be substituted with such groups, particularly with halogen atoms, methyl and methoxy groups and trifluoromethyl groups, with the expectation of producing pyridinium salts equivalent in activity to the other compounds described herein.

It will be understood that the present invention may be practiced in a number of different ways, making use of various subclasses of compounds within the scope of this invention. For example, the following subclasses of compounds are contemplated, both as new compositions of matter and for use in the herbicidal methods and compositions of this invention. Each numbered subparagraph below describes an independent subclass of compounds of the invention; in each subclass, the variable substituents have the general meanings above if not otherwise stated.

Compounds wherein:
1. $R^1$ represents halo;
2. $R^1$ represents methoxy or methylthio;
3. $R^1$ represents halo, methylthio or methoxy;
4. $R^1$ represents dimethylamino;
5. $R^2$ represents hydrogen, phenoxy, phenylthio, phenyl or substituted phenyl;
6. $R^2$ represents hydrogen, alkyl, alkoxy or alkylthio;
7. $R^2$ represents phenoxy, phenylthio, phenyl or substituted phenyl;
8. $R^2$ represents alkyl, alkoxy or alkylthio;
9. $R^2$ represents alkyl, phenyl or phenyl monosubstituted with chloro, bromo, fluoro, trifluoromethyl, methyl or methoxy;
10. $R^3$ represents methyl, methoxy, trifluoromethyl, chloro, fluoro or bromo;
11. the anion is halide, trifluoromethanesulfonate, methanesulfonate or toluenesulfonate;
12. the compounds as described by subparagraphs 1 and 5;
13. the compounds as described by subparagraphs 1 and 6;
14. the compounds as described by subparagraphs 1 and 7;
15. the compounds as described by subparagraphs 1 and 8;

16. the compounds as described by subparagraphs 1 and 9;
17. the compounds as described by subparagraphs 1 and 10;
18. the compounds as described by subparagraphs 1 and 11;
19. the compounds as described by subparagraphs 2 and 5;
20. the compounds as described by subparagraphs 2 and 6;
21. the compounds as described by subparagraphs 2 and 7;
22. the compounds as described by subparagraphs 2 and 8;
23. the compounds as described by subparagraphs 2 and 9;
24. the compounds as described by subparagraphs 2 and 10;
25. the compounds as described by subparagraphs 2 and 11;
26. the compounds as described by subparagraphs 3 and 5;
27. the compounds as described by subparagraphs 3 and 6;
28. the compounds as described by subparagraphs 3 and 7;
29. the compounds as described by subparagraphs 3 and 8;
30. the compounds as described by subparagraphs 3 and 9;
31. the compounds as described by subparagraphs 3 and 10;
32. the compounds as described by subparagraphs 3 and 11;
33. the compounds as described by subparagraphs 4 and 5;
34. the compounds as described by subparagraphs 4 and 6;
35. the compounds as described by subparagraphs 4 and 7;
36. the compounds as described by subparagraphs 4 and 8;
37. the compounds as described by subparagraphs 4 and 9;
38. the compounds as described by subparagraphs 4 and 10;
39. the compounds as described by subparagraphs 4 and 11;
40. the compounds as described by subparagraphs 5 and 10;
41. the compounds as described by subparagraphs 5 and 11;
42. the compounds as described by subparagraphs 6 and 10;
43. the compounds as described by subparagraphs 6 and 11;
44. the compounds as described by subparagraphs 7 and 10;
45. the compounds as described by subparagraphs 7 and 11;
46. the compounds as described by subparagraphs 8 and 10;
47. the compounds as described by subparagraphs 8 and 11;
48. the compounds as described by subparagraphs 9 and 10;
49. the compounds as described by subparagraphs 9 and 11;
50. the compounds as described by subparagraphs 10 and 11;
51. the compounds as described by subparagraphs 1, 5 and 10;
52. the compounds as described by subparagraphs 1, 6 and 10;
53. the compounds as described by subparagraphs 1, 7 and 10;
54. the compounds as described by subparagraphs 1, 8 and 10;
55. the compounds as described by subparagraphs 1, 9 and 10;
56. the compounds as described by subparagraphs 2, 5 and 10;
57. the compounds as described by subparagraphs 2, 6 and 10;
58. the compounds as described by subparagraphs 2, 7 and 10;
59. the compounds as described by subparagraphs 2, 8 and 10;
60. the compounds as described by subparagraphs 2, 9 and 10;
61. the compounds as described by subparagraphs 3, 5 and 10;
62. the compounds as described by subparagraphs 3, 6 and 10;
63. the compounds as described by subparagraphs 3, 7 and 10;
64. the compounds as described by subparagraphs 3, 8 and 10;
65. the compounds as described by subparagraphs 3, 9 and 10;
66. the compounds as described by subparagraphs 4, 5 and 10;
67. the compounds as described by subparagraphs 4, 6 and 10;
68. the compounds as described by subparagraphs 4, 7 and 10;
69. the compounds as described by subparagraphs 4, 8 and 10;
70. the compounds as described by subparagraphs 4, 9 and 10;
71. the compounds as described by subparagraphs 5, 10 and 11;
72. the compounds as described by subparagraphs 6, 10 and 11;
73. the compounds as described by subparagraphs 7, 10 and 11;
74. the compounds as described by subparagraphs 8, 10 and 11;
75. the compounds as described by subparagraphs 9, 10 and 11;
76. the compounds as described by subparagraphs 1, 5, 10 and 11;
77. the compounds as described by subparagraphs 1, 6, 10 and 11;
78. the compounds as described by subparagraphs 1, 7, 10 and 11;
79. the compounds as described by subparagraphs 1, 8, 10 and 11;
80. the compounds as described by subparagraphs 1, 9, 10 and 11;
81. the compounds as described by subparagraphs 2, 5, 10 and 11;
82. the compounds as described by subparagraphs 2, 6, 10 and 11;
83. the compounds as described by subparagraphs 2, 7, 10 and 11;

84. the compounds as described by subparagraphs 2, 8, 10 and 11;
85. the compounds as described by subparagraphs 2, 9, 10 and 11;
86. the compounds as described by subparagraphs 3, 5, 10 and 11;
87. the compounds as described by subparagraphs 3, 6, 10 and 11;
88. the compounds as described by subparagraphs 3, 7, 10 and 11;
89. the compounds as described by subparagraphs 3, 8, 10 and 11;
90. the compounds as described by subparagraphs 3, 9, 10 and 11;
91. the compounds as described by subparagraphs 4, 5, 10 and 11.
92. the compounds as described by subparagraphs 4, 6, 10 and 11;
93. the compoundds as described by subparagraphs 4, 7, 10 and 11;
94. the compounds as described by subparagraphs 4, 8, 10 and 11;
95. the compounds as described by subparagraphs 4, 9, 10 and 11;

A number of compounds typical of the invention will be named, to assure that agricultural chemists understand and can obtain the compounds of this invention.

4-chloro-1-ethyl-3-(4-fluorophenyl)-5-(3-propylphenyl)pyridinium sulfate 4-bromo-1-ethyl-3-(3-chlorophenyl)-5-(4-ethylphenyl)pyridinium chloride 4-methoxy-1-methyl-3-phenoxy-5-(3-trifluoromethylphenyl)pyridinium hydrogen sulfate 3-(3-ethoxyphenyl)-4-fluoro-1-methylpyridinium phosphate 4-dimethylamino-1-ethyl-3-phenylthio-5-(3-propoxyphenyl)pyridinium phenylsulfonate 3-ethoxy-1-ethyl-4-iodo-5-(3-isopropylphenyl)pyridinium fluoride 3-butoxy-1-ethyl-5-(3-fluorophenyl)-4-methylthiopyridinium nitrate 4-bromo-3-ethyl-1-methyl-5-(3-methylphenyl)pyridinium trifluoromethanesulfonate 4-chloro-1-ethyl-3-phenyl-5-(3-propylphenyl)pyridinium iodide 1-ethyl-3-(s-butylthio)-4-fluoro-5-(3-methoxyphenyl)pyridinium hydrogen phosphate 1-ethyl-3-(2-fluorophenyl)-4-dimethylamino-5-(3-trifluoromethylphenyl)pyridinium methanesulfonate 3-(3-bromophenyl)-4-dimethylamino-1-methylpyridinium p-toluenesulfonate 3-(3-ethylphenyl)-1-ethyl-4-methoxy-5-(2-propylphenyl)pyridinium potassium sulfate 3-(3-chlorophenyl)-1-ethyl-4-methylthio-5-phenoxypyridinium disodium phosphate 4-chloro-3-(3-fluorophenyl)-1-methyl-5-propylpyridinium bromide 4-bromo-3-methoxy-1-methyl-5-(3-propoxyphenyl)pyridinium hydrogen sulfate 3-(3-bromophenyl)-4-iodo-1-methyl-5-phenylthiopyridinium nitrate 3-(3-ethylphenyl)-4-fluoro-1-methylpyridinium bromide 4-bromo-3-(3-methylphenyl)-1-methyl-5-phenylthiopyridinium p-ethylphenylsulfonate 3-isopropylthio-4-methoxy-5-(3-methoxyphenyl)-1-methylpyridinium dihydrogen phosphate 3-(3-chlorophenyl)-5-(3-isopropoxyphenyl)-1-ethyl-4-methylthiopyridinium lithium sulfate 4-dimethylamino-1-ethyl-3-(3-ethoxyphenyl)-5-phenoxypyridinium ethanesulfonate 3-(2-bromophenyl)-5-(3-chlorophenyl)-4-dimethylamino-1-ethylpyridinium fluoride 3-(3-isopropoxyphenyl)-5-isopropyl-4-methoxy-1-methylpyridinium sulfate 4-chloro-1-ethyl-3-(3-ethylphenyl)pyridinium methanesulfonate 4-bromo-3-isobutyl-1-methyl-5-(3-trifluoromethylphenyl)pyridinium hydrogen phosphate 4-fluoro-3-(3-fluorophenyl)-5-(4-methylphenyl)-1-methylpyridinium dihydrogen phosphate 4-iodo-3-isobutyl-1-methyl-5-(3-propylphenyl)pyridinium potassium sulfate 1-methyl-4-methylthio-3-phenylthio-5-(3-propoxyphenyl)pyridinium phenylsulfonate 3-(3-bromophenyl)-5-(4-ethoxyphenyl)-4-fluoro-1-methylpyridinium nitrate 4-dimethylamino-3-(3-ethoxyphenyl)-1-ethyl-5-(3-isopropoxyphenyl)pyridinium fluoride 4-bromo-1-ethyl-3-(3-trifluoromethylphenyl)5-(4-trifluoromethylphenyl)pyridinium chloride 4-iodo-1,3-dimethyl-5-(3-propylphenyl)pyridinium phosphate 4-bromo-1-ethyl-3-(2-isopropylphenyl)-5-(3-isopropylphenyl)pyridinium phenylsulfonate 4-chloro-1-ethyl-3-(4-methoxyphenyl)-5-(3-trifluoromethylphenyl)pyridinium fluoride 1-ethyl-4-fluoro-3-(3-methylphenyl)-5-phenoxypyridinium chloride 1-ethyl-4-iodo-3-(3-isopropylphenyl)-5-(3-propoxyphenyl)pyridinium disodium phosphate 3-(t-butoxy)-1-ethyl-4-methoxy-5-(3-propoxyphenyl)pyridinium nitrate 3-butyl-1-ethyl-4-iodo-5-(3-trifluoromethylphenyl)pyridinium hydrogen phosphate 3-(t-butyl)-4-chloro-5-(3-ethylphenyl)-1-methylpyridinium m-ethylphenylsulfonate The compounds of this invention are made by processes which are modifications of known organic chemical methods. Most of the compounds are most readily made from correspondingly 3- and 5-substituted 4(1H)-pyridinones. Such pyridinones are the subject of U.S. Pat. No. 4,152,136 issued May 1, 1979, and the synthesis of such pyridinones is fully described in the patent. The disclosure of U.S. Pat. No. 4,152,136 is incorporated herein by reference as a teaching of how to prepare the starting materials used in the synthesis of the compounds of this invention.

The compounds of this invention wherein $R^1$ represents halo are easily made from the corresponding 1-unsubstituted 4(1H)-pyridinone. The 4-position of the pyridinone is first halogenated with any convenient halogenating agent, such as phosphorus oxychloride, phosgene, phosphorus pentachloride, phosphorus oxybromide, and the like. The halogenation goes best in the presence of a catalyst such as dimethylaniline or dimethylformamide. The halogenations are carried out in an inert solvent, such as chloroform, diethyl ether or simply in excess halogenating agent. Temperatures from 0° C. to 50° C. are appropriate but the reflux temperature of the reaction mixture is usually the best reaction temperature.

The nitrogen atom of the pyridine ring is then quaternized. Reagents such as methyl iodide, ethyl chloride, methyl bromide and ethyl fluoride readily react with the 4-halopyridine to form the desired pyridinium salts. Usually, the reactions are carried out at room temperature although elevated temperatures up to the reflux temperature of the mixture are satisfactory. Inert reaction solvents including the halogenated solvents, the alcohols, the ethers and the like may be used. Other useful alkylating agents include methyl trifluoromethanesulfonate, methyl fluorosulfonate, methyl methanesulfonate, methyl p-toluenesulfonate and dimethyl sulfate. The nitrate salt may be obtained from a halide salt and silver nitrate.

The compounds having 4-methoxy and methylthio groups are most readily made from the corresponding 1-substituted pyridinone or pyridinethione. The starting compound is reacted with a methylating agent to form the pyridinium derivative. For example, methyl trifluoromethanesulfonate is a particularly useful methylating agent, producing trifluoromethanesulfonate pyridinium salts.

The formiminium halide route for the preparation of pyridinone starting compounds is particularly useful. A Villsmeier reagent prepared from dimethylformamide and phosgene is used. A solvent is generally used in the reaction of the starting 2-propanone with the Villsmeier reagent, and brief reaction times at the reflux temperature of the reaction mixture are appropriate. The aminoformylated propanone is then reacted with ammonia or ammonium hydroxide to form the 1-unsubstituted pyridine having either a 4-chloro or a 4-dimethylamino substituent. Some of each product is usually formed. The 1-unsubstituted pyridine is then N-alkylated as described above.

The various reaction steps described above are carried out in the usual inert reaction solvents. No catalysts or unusual operating conditions are required. Alkanes such as hexane, aromatics such as benzene and toluene, ethers such as tetrahydrofuran, diethyl ether and diisopropyl ether, and halogenated solvents such as chloroform and methylene chloride are all appropriate. The alkylation steps are particularly advantageously performed in chloroform.

The following specific preparative examples are provided as assistance to the chemist, to assure that all of the compounds of this invention are readily accessible.

In the examples below, the products were identified by elemental microanalysis, thin layer chromatography, nuclear magnetic resonance analysis, infrared analysis, ultraviolet analysis and mass spectroscopy as was required or convenient in each case.

All temperatures in the examples below are on the Celsius scale.

EXAMPLE 1

4-methoxy-1-methyl-3-phenyl-5-(3-trifluoromethylphenyl)-pyridinium trifluoromethanesulfonate A 556 g. portion of 1-phenyl-3-(3-trifluoromethylphenyl)-2-propanone was added to 4000 ml. of tetrahydrofuran containing 284 g. of sodium methoxide at 10°–15°. The addition was carried out over a 20 minute period with constant stirring while the temperature was held below 15°, and the mixture was then stirred for 15 minutes more. Then 370 g. of ethyl formate was added over a 30 minute period, and the complete mixture was stirred 1 hour more at 10°–15°. A second portion of 296 g. of ethyl formate was then added slowly and the mixture was stirred overnight while it was allowed to warm to room temperature.

A solution of 336 g. of methylamine hydrochloride in 1300 ml. of water was then added, and the mixture was stirred for ½ hour more. The phases were then allowed to separate, and the organic layer was concentrated under vacuum. The residue was dissolved in methylene chloride, dried over sodium sulfate and concentrated to an oil, which weighed 723 g.

The oil was added to 4000 ml. of tetrahydrofuran, 284 g. of sodium methoxide was added, and the process described above was repeated, using the same weights of ethyl formate and of methylamine hydrochloride. The oily residue obtained from evaporation of the reaction mixture was dissolved in methylene chloride, washed with water and dried over sodium sulfate. The methylene chloride was evaporated under vacuum, and the residue crystallized upon standing. A small amount of diethyl ether was added to form a thick slurry which was chilled overnight. Filtration of the chilled slurry produced 430 g. of 1-methyl-3-phenyl-5-(3-trifluoromethylphenyl)-4(1H)-pyridinone, m.p. 153°.

A 3.2 g. portion of the above intermediate pyridinone was combined with 1.8 g. of methyl trifluoromethanesulfonate in 50 ml. of methylene chloride. The mixture was allowed to stand for 3 days, and was then evaporated under vacuum to a glassy residue. The residue was taken up in chloroform and recrystallized by the addition of diethyl ether to produce 4-methoxy-1-methyl-3-phenyl-5-(3-trifluoromethylphenyl)pyridinium trifluoromethanesulfonate, m.p. 126°–127°.

|   | Theoretical | Found |
|---|---|---|
| C | 51.12% | 50.42% |
| H | 3.47 | 3.72 |
| N | 2.84 | 2.94 |

EXAMPLE 2

3-(3-bromophenyl)-4-methoxy-1-methyl-5-phenylpyridinium trifluoromethanesulfonate A 10 g. portion of 3-(3-bromophenyl)-1-methyl-5-phenyl-4(1H)-pyridinone was made from 22 g. of the corresponding 2-propanone as described in Example 1. A 3.4 g. portion of the intermediate pyridinone was dissolved in chloroform and 1.8 g. of methyl trifluoromethanesulfonate was added. The reaction mixture was allowed to stand overnight, and the volatile portions were then evaporated under vacuum. The residue was identified as 3-(3-bromophenyl)-4-methoxy-1-methyl-5-phenylpyridinium trifluoromethanesulfonate, molecular weight 339 by mass spectroscopy.

|   | Theoretical | Found |
|---|---|---|
| C | 47.36% | 47.42% |
| H | 3.40 | 3.54 |
| N | 2.78 | 3.05 |

EXAMPLE 3

4-chloro-3-(3-chlorophenyl)-5-(4-chlorophenyl)-1-methylpyridinium iodide

A 10 g. portion of 1-(-3-chlorophenyl)-3-(4-chlorophenyl)-2-propanone was reacted with 20 ml. of dimethylformamide dimethylacetal overnight at reflux temperature. In the morning, volatile portions of the reaction mixture were removed under vacuum, and the residue was dissolved in 50 ml. of denatured ethanol. Twenty ml. of concentrated ammonium hydroxide was added to the ethanol solution, and the mixture was refluxed for 6 hours. The alkaline mixture was cooled and filtered, and the solid product was thoroughly washed with chloroform to produce 10 g. of 3-(3-chlorophenyl)-5-(4-chlorophenyl)-4(1H)-pyridinone.

Eight g. of the pyridinone was combined with 25 ml. of phosphorus oxychloride and 1 ml. of dimethylformamide, and was stirred at reflux temperature for 3 hours. Volatile materials were then removed from the mixture under vacuum, and the residue was dissolved in chloroform and poured into a large amount of water. The organic layer was separated, washed with water and evaporated to dryness under vacuum. The residue was recrystallized from chloroform-hexane to produce 4 g. of 4-chloro-3-(3-chlorophenyl)-5-(4-chlorophenyl)pyridine.

A 2 g. portion of the above pyridine was dissolved in 10 ml. of chloroform, and 10 ml. of methyl iodide was added. The mixture was allowed to stand at room temperature for 4 days. The reaction mixture was filtered, and the solids were washed with chloroform-hexane. The dried washed product was identified as 4-chloro-3-(3-chlorophenyl)-5-(4-chlorophenyl)-1-methyl-pyridinium iodide, m.p. 214°–217°, yield 2.1 g.

|   | Theoretical | Found |
|---|---|---|
| C | 45.37% | 45.56% |
| H | 2.75 | 2.92 |
| N | 2.94 | 3.07 |

EXAMPLE 4

4-chloro-3-(3-fluorophenyl)-1-methyl-5-phenyl-pyridinium iodide

Twelve g. of 1-(3-fluorophenyl)-3-phenyl-2-propanone was reacted with dimethylformamide dimethylacetal and ammonium hydroxide as in Example 3 to prepare 8.6 g. of 3-(3-fluorophenyl)-5-phenyl-4(1H)-pyridinone.

A 7.5 g. portion of the pyridinone was chlorinated with 25 ml. of phosphorus oxychloride in the presence of 1.5 ml. of dimethylformamide as in Example 3 to produce 2.5 g. of 4-chloro-3-(3-fluorophenyl)-5-phenylpyridine.

Two g. of the chloropyridine was mixed with 10 ml. of methyl iodide in 50 ml. of chloroform and allowed to stand for 5 days. The volatile portions of the mixture were then removed under vacuum, and the solid residue was crystallized from chloroform-diethyl ether. The product was identified as 2.5 g. of 4-chloro-3-(3-fluorophenyl)-1-methyl-5-phenylpyridinium iodide, m.p. 195°–197°.

|   | Theoretical | Found |
|---|---|---|
| C | 50.79% | 50.71% |
| H | 3.32 | 3.23 |
| N | 3.29 | 3.58 |

EXAMPLE 5

4-chloro-3-(4-chlorophenyl)-1-methyl-5-(3-trifluoromethylphenyl)pyridinium iodide Following the scheme of Example 3, 12 g. of 1-(4-chlorophenyl)-3-(3-trifluoromethylphenyl)-2-propanone was reacted with dimethylformamide dimethyl acetal and ammonium hydroxide to form 8 g. of the corresponding 1-unsubstituted pyridinone. Seven g. of the pyridinone was chlorinated with phosphorus oxychloride to prepare 5.4 g. of the corresponding 4-chloropyridine, 2 g. of which was alkylated and quaternized with 10 ml. of methyl iodide to obtain 1.5 g. of 4-chloro-3-(4-chlorophenyl)-1-methyl-5-(3-trifluoromethylphenyl)-pyridinium iodide, m.p. 251°–254°.

|   | Theoretical | Found |
|---|---|---|
| C | 44.74% | 44.99% |
| H | 2.57 | 2.49 |
| N | 2.75 | 2.89 |

EXAMPLE 6

4-chloro-1-methyl-3-phenyl-5-(3-trifluoromethylphenyl)-pyridinium iodide

The scheme of Example 3 was used, starting with 14 g. of 1-phenyl-3-(3-trifluoromethylphenyl)-2-propanone which was cyclized with dimethylformamide dimethyl acetal and ammonium hydroxide to prepare 9.7 g. of 3-phenyl-5-(3-trifluoromethylphenyl)-4(1H)-pyridinone. Eight grams of the pyridinone was chlorinated with phosphorus oxychloride to obtain 3 g. of the corresponding 4-chloropyridine, of which 2 g. was reacted with methyl iodide to prepare 1 g. of 4-chloro-1-methyl-3-phenyl-5-(3-trifluoromethylphenyl)-pyridinium iodide, m.p. 184°–186°.

|   | Theoretical | Found |
|---|---|---|
| C | 49.40% | 48.90% |
| H | 3.03 | 3.15 |
| N | 3.03 | 3.21 |

EXAMPLE 7

4-chloro-3,5-bis(3-chlorophenyl)-1-methylpyridinium iodide

The scheme of Example 3 was again used, starting with 8 g. of 1,3-bis(3-chlorophenyl)-2-propanone and dimethylformamide dimethyl acetal and ammonium hydroxide to prepare 4.5 g. of 3,5-bis(3-chlorophenyl)-4(1H)-pyridinone. Chlorination of the pyridinone with phosphorus oxychloride produced 1.8 g. of the corresponding 4-chloropyridine, of which 1.5 g. was alkylated and quaternized with methyl iodide to prepare 1.2 g. of 4-chloro-3,5-bis(3-chlorophenyl)-1-methylpyridinium iodide, m.p. 215°–218° C.

|   | Theoretical | Found |
|---|---|---|
| C | 45.37% | 45.66% |
| H | 2.75 | 2.81 |
| N | 2.94 | 3.12 |

EXAMPLE 8

4-chloro-1-ethyl-3-(3-methylphenyl)-5-phenyl-pyridinium iodide

Following the scheme of Example 3 again, 12 g. of 1-(3-methylphenyl)-3-phenyl-2-propanone was converted to 8.1 g. of 3-(3-methylphenyl)-5-phenyl-4(1H)-pyridinone by reaction with dimethylformamide dimethyl acetal and ammonium hydroxide. A 7.5 g. portion of the pyridinone was chlorinated with phosphorus oxychloride to prepare 4.2 g. of the corresponding 4-chloropyridine, and 2 g. of the chloropyridine was reacted with 10 ml. of ethyl iodide in chloroform to prepare 0.4 g. of 4-chloro-1-ethyl-3-(3-methylphenyl)-5-phenylpyridinium iodide, m.p. 191°–194°.

|   | Theoretical | Found |
|---|---|---|
| C | 55.13% | 54.86% |
| H | 4.40 | 4.33 |
| N | 3.21 | 3.30 |

EXAMPLE 9

4-bromo-1-methyl-3-phenyl-5-(3-trifluoromethylphenyl)-pyridinium iodide

A 10 g. portion of 1-hydroxy-4-phenyl-2-(3-trifluoromethylphenyl)-1-butene-3-one was heated with 20 ml. of dimethylformamide dimethyl acetal for 12 hours at steam bath temperature. Volatile substances were then removed under vacuum and the residue was dissolved in 50 ml. of denatured ethanol and 20 ml. of concentrated ammonium hydroxide. The mixture was stirred at reflux temperature for 6 hours. The solids were filtered from the cooled reaction mixture and were washed with chloroform. The solids, 4 g. of 3-phenyl-5-(3-trifluoromethylphenyl)-4(1H)-pyridinone, were combined with 3.6 g. of phosphorus oxybromide in dimethylformamide and the mixture was stirred at steam bath temperature for 5 hours. The mixture was then poured over ice and filtered to obtain 1.7 g. of 4-bromo-3-phenyl-5-(3-trifluoromethylphenyl)pyridine.

A 1.5 g. portion of the bromopyridine was reacted with 7 ml. of methyl iodide as in Example 3 to prepare 1.2 g. of 4-bromo-1-methyl-3-phenyl-5-(3-trifluoromethylphenyl)pyridinium iodide, m.p. 173°–176°.

|   | Theoretical | Found |
|---|---|---|
| C | 43.88% | 43.85% |
| H | 2.71 | 2.64 |
| N | 2.69 | 2.60 |

EXAMPLE 10

4-methoxy-3-(3-methoxyphenyl)-1-methyl-5-phenylpyridinium trifluoromethanesulfonate A 9.96 g. portion of 3-methoxyphenyl acetic acid was converted to the acid chloride by reaction with oxalyl chloride on the steam bath for 30 minutes. The acid chloride was dissolved in diethyl ether and added dropwise to a diethyl ether solution of 10.3 g. of N,N-diethylstyrylamine containing 5 g. of pyridine at 0° under a nitrogen blanket. The reaction mixture was stirred at 0° for 2 hours after the addition was complete. The mixture was then filtered, and the filtrate was evaporated under vacuum to produce 12 g. of 1-diethylamino-4-(3-methoxyphenyl)-2-phenyl-1-buten-3-one.

The butenone was combined with 12 g. of dimethylformamide dimethyl acetal and was stirred at reflux temperature for 12 hours. Volatile materials were then removed under vacuum. The residue was dissolved in 50 ml. of methanol, and 12 g. of methylamine hydrochloride was added. The methanol solution was stirred at reflux temperature for 12 hours, and was then evaporated under vacuum. The residue was purified by column chromatography over silica gel using 1:1 benzene:ethyl acetate. The purified intermediate product was 1.7 g. of 3-(3-methoxyphenyl)1-methyl-5-phenyl-4(1H)-pyridinone.

The pyridinone was combined with 3 g. of methyl trifluoromethanesulfonate in 25 ml. of chloroform and allowed to stand at room temperature for 7 days. The solvent was then evaporated, and the product was crystallized from chloroform-hexane to obtain 1.2 g. of 4-methoxy-3-(3-methoxyphenyl)-1-methyl-5-phenylpyridinium trifluoromethanesulfonate, m.p. 139°–142°.

|   | Theoretical | Found |
|---|---|---|
| C | 55.38% | 55.53% |
| H | 4.43 | 4.42 |
| N | 3.08 | 3.02 |

EXAMPLE 11

4-bromo-3-(3-chlorophenyl)-5-(4-chlorophenyl)-1-methylpyridinium iodide

The procedures of Example 3 were followed. A 4 g. portion of the intermediate 4(1H)-pyridinone of Example 3 was brominated with phosphorus oxybromide to produce 1.4 g. of the corresponding 4-bromopyridine, of which 1 g. was reacted with methyl iodide to produce 0.4 g. of 4-bromo-3-(3-chlorophenyl)-5-(4-chlorophenyl)-1-methylpyridinium iodide, m.p. 175°–180°.

|   | Theoretical | Found |
|---|---|---|
| C | 41.49% | 41.25% |
| H | 2.52 | 2.54 |
| N | 2.69 | 2.65 |

EXAMPLE 12

4-bromo-1-ethyl-3-phenyl-5-(3-trifluoromethylphenyl)-pyridinium iodide

EXAMPLE 13

1-ethyl-4-iodo-3-phenyl-5-(3-trifluoromethylphenyl)-pyridinium iodide

A 2 g. portion of the 4-bromopyridine intermediate of Example 9 was combined with 10 ml. of ethyl iodide and allowed to stand at room temperature for 3 days. Volatile materials were then evaporated under vacuum, and the solids were crystallized from chloroform-hexane, yield 0.25 g., m.p. 235°–238°. Analysis by nuclear magnetic resonance and mass spectrometry techniques identified the product as consisting of approximately 60 percent of the compound of Example 12, and approximately 40 percent of the compound of Example 13.

EXAMPLE 14

3-(3-bromophenyl)-1-methyl-4-methylthio-5-phenylpyridinium trifluoromethanesulfonate Five g. of the intermediate 4(1H)-pyridinone of Example 2 was reacted with 5 g. of phosphorus pentasulfide in pyridine for 2 hours at reflux temperature. The reaction mixture was then poured slowly into water, and the aqueous mixture was filtered. The solids were air dried and crystallized from denatured ethanol to obtain 3.1 g. of 3-(3-bromophenyl)-1-methyl-5-phenylpyridinethione. A 1 g. portion of the thione was mixed with 5 ml. of methyl trifluoromethanesulfonate and allowed to stand at room temperature for 4 days. The mixture was then evaporated to dryness under vacuum and the residue was crystallized from chloroform-hexane to obtain 1.1 g. of 3-(3-bromophenyl)1-methyl-4-methylthio-5-phenylpyridinium trifluoromethanesulfonate, m.p. 165°–168°.

|   | Theoretical | Found |
|---|---|---|
| C | 46.15% | 46.61% |
| H | 3.27 | 3.43 |
| N | 2.69 | 2.66 |

EXAMPLE 15

1-methyl-4-methylthio-3-phenyl-5-(3-trifluoromethylphenyl)-pyridinium trifluoromethanesulfonate Five g. of the intermediate 1-methyl-4(1H)-pyridinone of Example 1 was reacted with 5 g. of phosphorus pentasulfide in 50 ml. of pyridine as described in Example 14 to produce 3.6 g. of 1-methyl-3-phenyl-5-(3-trifluoromethylphenyl)-4(1H)-pyridinethione. A 1.5 g. portion of the pyridinethione was reacted with 4 ml. of methyl trifluoromethanesulfonate as described in Example 14 to prepare 1.3 g. of 1-methyl-4-methylthio-3-phenyl-5-(3-trifluoromethylphenyl)pyridinium trifluoromethanesulfonate, m.p. 157°–159°.

|   | Theoretical | Found |
|---|---|---|
| C | 49.51% | 49.65% |
| H | 3.36 | 3.43 |
| N | 2.75 | 2.72 |

EXAMPLE 16

4-chloro-1,3-diethyl-5-(3-trifluoromethylphenyl)-pyridinium iodide

A Villsmeier reagent was prepared from 20 g. of phosgene and 15 g. of dimethylformamide in chloroform. A 24 g. portion of 1-(3-trifluoromethylphenyl)-2-pentanone was added, and the mixture was stirred at reflux temperature for 30 minutes. Eighty ml. of concentrated ammonium hydroxide was then added, and the mixture was stirred on the steam bath to evaporate chloroform. About 50 ml. of additional ammonium hydroxide was then added, and the mixture was stirred on the steam bath for 30 minutes more. The reaction mixture was then cooled, and extracted with diethyl ether. The ether layer was washed with water, dried over magnesium sulfate, and evaporated under vacuum. The residue was first chromatographed over a silica gel column with 10 percent ethyl acetate in benzene. The fourth fraction was rechromatographed over alumina with 50 percent ethyl acetate in benzene. The second fraction was freed of solvent under vacuum to produce 5.5 g. of 4-chloro-3-ethyl-5-(3-trifluoromethylphenyl)-pyridine, an oily liquid.

A 2 g. portion of the above chloropyridine was reacted with ethyl iodide at room temperature to prepare 1.5 g. of 4-chloro-1,3-diethyl-5-(3-trifluoromethylphenyl)-pyridinium iodide. m.p. 138°–139°.

|   | Theoretical | Found |
|---|---|---|
| C | 43.51% | 43.79% |
| H | 3.65 | 3.79 |

-continued

|   | Theoretical | Found |
|---|---|---|
| N | 3.17 | 3.21 |

EXAMPLE 17

4-dimethylamino-3-ethyl-1-methyl-5-(3-trifluoromethylphenyl)-pyridinium iodide

The third fraction from the chromatography over alumina in Example 16 was concentrated and found to consist of 3 g. of 4-dimethylamino-1-ethyl-5-(3-trifluoromethylphenyl)pyridine. The intermediate was dissolved in chloroform and reacted with methyl iodide at room temperature to prepare 4-dimethylamino-3-ethyl-1-methyl-5-(3-trifluoromethylphenyl)pyridinium iodide, m.p. 138°–139°.

|   | Theoretical | Found |
|---|---|---|
| C | 43.51% | 43.79% |
| H | 3.65 | 3.79 |
| N | 3.17 | 3.21 |

EXAMPLE 18

4-dimethylamino-1-methyl-3-phenyl-5-(3-trifluoromethylphenyl)pyridinium iodide

A 28 g. portion of 1-phenyl-3-(3-trifluoromethylphenyl)-2-propanone was reacted with a Villsmeier reagent, formed from 45 g. of phosphorus oxychloride and 22 ml. of dimethylformamide, at reflux temperature in chloroform for 1½ hours. The mixture was then reacted with ammonium hydroxide as described in Example 16. The oily product was purified over a silica gel column with 20 percent ethyl acetate in benzene to produce 6.5 g. of 4-dimethylamino-3-phenyl-5-(3-trifluoromethylphenyl)pyridine.

Two g. of the intermediate pyridine was reacted with methyl iodide in chloroform at room temperature overnight. The mixture was then evaporated to dryness under vacuum, and the residue was triturated in diethyl ether. The solids were taken up in acetone, and crystallized in the freezer to produce 0.5 g. of 4-dimethylamino-1-methyl-3-phenyl-5-(3-trifluoromethylphenyl)pyridinium iodide, m.p. 173°–175°.

|   | Theoretical | Found |
|---|---|---|
| C | 52.08% | 52.13% |
| H | 4.16 | 3.90 |
| N | 5.78 | 5.57 |

EXAMPLE 19

5-(3-bromophenyl)-4-methoxy-1-methyl-3-phenylpyridinium methanesulfonate

A mixture of 4.0 g. of 5-(3-bromophenyl)-1-methyl-3-phenyl-4(1H)-pyridinone and 20 ml. of methyl methanesulfonate in benzene was heated under reflux for 6 hours. The mixture was cooled and the solvent removed in vacuo. The product failed to crystallize. The product was passed over a silica gel column in ethyl acetate. After the front-running spot was removed the column was flushed with ethanol. The ethanol fractions were again placed on a silica gel solumn and front-running impurities removed. The column was flushed with ethanol and the ethanol removed to yield 0.75 g. of a hard glass. The nmr spectrum of the product was consistent with the structure of the expected salt. For example, there was an N-CH$_3$ peak at 4.4 ppm and a peak at 8.7 ppm attributed to the hydrogens at the 2- and 6-positions of the pyridine ring. As is characteristic of pyridinium salts, both these peaks were shifted from the corresponding peaks in the starting pyridinone.

EXAMPLE 20

4-ethylthio-1-methyl-3-phenyl-5-(3-trifluoromethylphenyl)pyridinium iodide

A mixture of 2.0 g. of 1-methyl-3-phenyl-5-(3-trifluoromethylphenyl)-4(1H)-pyridinethione in 10 ml. of ethyl iodide was heated on a steam bath for 10 minutes (until solution occurred). The mixture was then allowed to stand at room temperature for 3 days. The precipitate which formed was collected to yield 2.7 g. of 4-ethylthio-1-methyl-3-phenyl-5-(3-trifluoromethylphenyl)pyridinium iodide, m.p. 140°-143°.

|   | Theoretical | Found |
|---|---|---|
| C | 50.31% | 50.12% |
| H | 3.82 | 3.94 |
| N | 2.79 | 2.62 |

EXAMPLE 21

3-(4-chlorophenyl)-4-methoxy-1-methyl-5-(3-trifluoromethylphenyl)pyridinium fluorosulfonate To a solution of 2.0 g. of 3-(4-chlorophenyl)-1-methyl-5-(3-trifluoromethylphenyl)-4(1H)-pyridinone in 15 ml. of chloroform was added 5.0 ml. of methyl fluorosulfonate and the mixture was allowed to stand at room temperature for 2 days. The solvent was removed in vacuo and the residue was dissolved in chloroform and the solution washed with water. The chloroform was removed and the residue was crystallized from chloroform-hexane to obtain 0.4 g. of product, m.p. 224°-227°.

|   | Theoretical | Found |
|---|---|---|
| C | 47.78% | 51.29% |
| H | 3.06 | 3.70 |
| N | 2.65 | 2.93 |

EXAMPLE 22

4-iodo-1-methyl-3-phenyl-5-(3-trifluoromethylphenyl)-pyridinium iodide

A mixture of 1.0 g. of the product from Example 9 and 2.0 g. of sodium iodide in dimethylformamide was heated on a steam bath for 4 hours and was then poured into water. The precipitate that formed was removed and discarded. Upon standing, the desired compound precipitated from the aqueous solution. It was collected by filtration to yield 0.155 g. of 4-iodo-1-methyl-3-phenyl-5-(3-trifluoromethylphenyl)-pyridinium iodide, m.p. 220-224.

|   | Theoretical | Found |
|---|---|---|
| C | 40.24% | 40.49% |
| H | 2.49 | 2.61 |
| N | 2.47 | 2.46 |

EXAMPLE 23

1-methyl-4-methylthio-3-phenyl-5-(3-trifluoromethylphenyl)pyridinium methanesulfonate A mixture of 20 g. of 1-methyl-3-phenyl-5-(3-trifluoromethylphenyl)-4(1H)-pyridinethione and 6.0 g. of methyl methanesulfonate in benzene was heated under reflux overnight (about 16 hours). The solvent was removed in vacuo and the residue was crystallized from chloroformether to yield 1.9 g. of 1-methyl-4-methylthio-3-phenyl-5-(3-trifluoromethylphenyl)pyridinium methanesulfonate, m.p. 154°-157°.

|   | Theoretical | Found |
|---|---|---|
| C | 55.37% | 55.60% |
| H | 4.43 | 4.20 |
| N | 3.07 | 3.32 |

EXAMPLE 24

4-isopropylthio-1-methyl-3-phenyl-5-(3-trifluoromethylphenyl)pyridinium bromide

A mixture of 2.0 g. of 1-methyl-3-phenyl-5-(3-trifluoromethylphenyl)-4(1H)-pyridinethione and 20 ml. of 2-bromopropane in benzene was heated under reflux overnight. The residue was crystallized from chloroform-hexane to yield 1.5 g. of 4-isopropylthio-1-methyl-3-phenyl-5-(3-trifluoromethylphenyl)pyridinium bromide, m.p. 71°-74°.

EXAMPLE 25

4-methoxy-1-methyl-3-(3-methylphenyl)-5-(3-trifluoromethylphenyl)pyridinium fluorosulfonate A mixture of 2.0 g. of 1-methyl-3-(3-methylphenyl)-5-(3-trifluoromethylphenyl)-4(1H)-pyridinone and 5 ml. of methyl fluorosulfonate was allowed to stand at room temperature for 2 days. Excess methyl fluorosulfonate was removed in vacuo and the residue taken up in chloroform. The chloroform solution was washed 3 times with water and dried over magnesium sulfate. The chloroform was removed in vacuo and the residue crystallized from chloroform-ether to yield 0.8 g. of 4-methoxy-1-methyl-3-(3-methylphenyl)-5-(3-trifluoromethylphenyl)pyridinium fluorosulfonate, m.p. 123°-126°.

EXAMPLE 26

4-methoxy-1-methyl-3-phenoxy-5-(3-trifluoromethylphenyl)pyridinium fluorosulfonate To a solution of 2.0 g. of 1-methyl-3-phenoxy-5-(3-trifluoromethylphenyl)-4(1H)-pyridinone in 10 ml. of chloroform was added to 4.0 ml. of methyl fluorosulfonate and the mixture was allowed to stand at room temperature for 4 days. The mixture was washed with water and the chloroform removed in vacuo to yield 1.2 g. of an oil identified as 4-methoxy-1-methyl-3-phenoxy-5-(3-trifluoromethylphenyl)pyridinium fluorosulfonate. Attempts to crystallize the product failed.

EXAMPLE 27

4-methoxy-1-methyl-3-phenyl-5-(3-trifluoromethylphenyl)-pyridinium methanesulfonate A mixture of 2.5 g. of 1-methyl-3-phenyl-5-(3-trifluoromethylphenyl)-4(1H)-pyridinone and 10 ml. of methyl methanesulfonate in 100 ml. of benzene was heated under reflux for 2 days. The mixture was cooled and the benzene removed in vacuo to give an oil which solidified from ether-acetone to yield 1.5 g. of 4-methoxy-1-methyl-3-phenyl-5-(3-trifluoromethylphenyl)pyridinium methanesulfonate, m.p. 55°–59°.

|   | Theoretical | Found  |
|---|-------------|--------|
| C | 57.40%      | 57.22% |
| H | 4.59        | 4.68   |
| N | 3.19        | 3.21   |

EXAMPLE 28

4-bromo-5-(3-bromophenyl)-1-methyl-3-phenylpyridinium iodide

To 1.0 g. of 4-bromo-5-(3-bromophenyl)-3-phenylpyridine was added 5 ml. of methyl iodide. An oil began to form after about 1 hour. After standing overnight the excess methyl iodide had evaporated to leave a yellow solid which was recrystallized from chloroform-hexane to yield 1.1 g. of 4-bromo-5-(3-bromophenyl)-1-methyl-3-phenylpyridinium iodide, m.p. 184°–187°.

|   | Theoretical | Found  |
|---|-------------|--------|
| C | 40.71%      | 40.90% |
| H | 2.66        | 2.56   |
| N | 2.64        | 2.64   |

EXAMPLE 29

4-benzylthio-1-methyl-3-phenyl-5-(3-trifluoromethylphenyl)-pyridinium chloride A mixture of 2.0 g. of 1-methyl-3-phenyl-5-(3-trifluoromethylphenyl)-4(1H)-pyridinethione and 10 ml. of benzyl chloride in benzene was heated under reflux for 6 hours. The mixture was cooled and the benzene was removed in vacuo. The residue was put on a silica gel column in benzene and the column was flushed with benzene. The product was then removed from the column with denatured ethanol. The ethanol was removed and the residue was crystallized from ether yielding 0.7 g. of 4-benzylthio-1-methyl-3-phenyl-5-(3-trifluoromethylphenyl)pyridinium chloride, m.p. 70°–73°.

EXAMPLE 30

1-methyl-4-methylthio-3-n-propyl-5-(3-trifluoromethylphenyl)pyridinium iodide A solution of 1.0 g. of 1-methyl-3-n-propyl-5-(3-trifluoromethylphenyl)-4(1H)-pyridinethione and 3.0 ml. of methyl iodide was heated on a steam bath for ½ hour. The mixture was cooled and the solid product was collected by filtration. The product was crystallized from chloroform-hexane to yield 0.7 g. of 1-methyl-4-methylthio-3-n-propyl-5-(3-trifluoromethylphenyl)-pyridinium iodide, m.p. 76°–80°.

|   | Theoretical | Found  |
|---|-------------|--------|
| C | 45.04%      | 44.76% |
| H | 4.22        | 4.03   |
| N | 3.09        | 3.20   |

The compounds described above have been tested in a number of herbicidal test systems to determine the range of their herbicidal efficacy. The results produced by the compounds in the representative tests reported below are exemplary of the outstanding activity of the compounds.

Compound application rates are expressed in kilograms of the compound per hectare of land (kg./ha.) throughout this document.

Blank spaces in the tables below indicate that the compound was not tested against the named species. In some instances, the results of testing a compound repeatedly against a plant species have been averaged.

Untreated control plants or plots were included in all tests. Ratings of the control produced by the compounds were made by comparison of the treated plants or plots with the controls.

Test 1 broad spectrum greenhouse test

Square plastic pots were filled with a sterilized sandy loam soil and were planted to seeds of tomato, large crabgrass and pigweed. Each pot was individually fertilized.

Test compounds were applied postemergence to some pots and preemergence to others. Postemergence applications of the compounds were sprayed over the emerged plants about 12 days after the seeds were planted. Preemergence applications were sprayed on the soil the day after the seeds were planted.

Each test compound was dissolved in 1:1 acetone:ethanol at the rate of 2 g. per 100 ml. The solution also contained about 2 g. per 100 ml. of an anionic-nonionic surfactant blend. One ml. of the solution was diluted to 4 ml. with deionized water, and 1½ ml. of the resulting solution was applied to each pot, resulting in an application rate of 16.8 kg./ha. of test compound.

After the compounds were applied, the pots were moved to the greenhouse, watered as necessary, and observed and rated about 10–13 days after application of the compounds. Untreated control plants were used as standards in every test.

The table below reports results of testing typical compounds of the invention. The compounds are identified by their example numbers above.

Herbicidal effect was rated on a 1–5 scale, where 1 indicates normal plants, and 5 indicates death of the plants or no emergence.

Table 1

| Compound of Example No. | Preemergence | | | Postemergence | | |
|---|---|---|---|---|---|---|
|   | Tomato | Crabgrass | Pigweed | Tomato | Crabgrass | Pigweed |
| 3 | 4 | 5 | 5 | 4 | 5 | 5 |
| 7 | 3 | 4 | 4 | 3 | 4 | 3 |

Table 1-continued

| Compound of Example No. | Preemergence | | | Postemergence | | |
|---|---|---|---|---|---|---|
| | Tomato | Crabgrass | Pigweed | Tomato | Crabgrass | Pigweed |
| 9 | 5 | 5 | 5 | 4 | 3 | 3 | testing against the species named below were as follows.

Table 2

| Compound of Example No. | Preemergence | | | | | | | Postemergence | | | | | | |
|---|---|---|---|---|---|---|---|---|---|---|---|---|---|---|
| | Corn | Large Crabgrass | Pigweed | Foxtail | Velvetleaf | Morningglory | Zinnia | corn | Large Crabgrass | Pigweed | Foxtail | Velvetleaf | Morningglory | Zinnia |
| 1 | 2 | 5 | 5 | 4 | 4 | 4 | 2 | 4 | 4 | 4 | 4 | 4 | 3 | 2 |
| 2 | 2 | 4 | 4 | 4 | 3 | 4 | 2 | 3 | 3 | 3 | 3 | 3 | 3 | 2 |
| 3 | 2 | 5 | 5 | 5 | 4 | 2 | 2 | 2 | 2 | 2 | 2 | 2 | 2 | 2 |
| 4 | 2 | 4 | 3 | 4 | 3 | 3 | 2 | 2 | 2 | 3 | 2 | 2 | 2 | 2 |
| 5 | 2 | 4 | 5 | 5 | 4 | 3 | 2 | 2 | 2 | 2 | 2 | 2 | 2 | 2 |
| 6 | 3 | 5 | 4 | 5 | 4 | 2 | 3 | 2 | 3 | 3 | 2 | 2 | 2 | 2 |
| 7 | 3 | 5 | 4 | 4 | 3 | 2 | 1 | 2 | 2 | 2 | 3 | 3 | 2 | 2 |
| 8 | 2 | 2 | 2 | 4 | 2 | 2 | 1 | 1 | 1 | 2 | 1 | 2 | 1 | 1 |
| 10 | 1 | 3 | 2 | 3 | 2 | 2 | 2 | 3 | 2 | 2 | 3 | 3 | 3 | 3 |
| 11 | 2 | 5 | 4 | 5 | 4 | 3 | 2 | 2 | 2 | 3 | 3 | 3 | 2 | 2 |
| 19 | 4 | 5 | 5 | 4 | 4 | 4 | 3 | 3 | 3 | 4 | 3 | 3 | 2 | 3 |
| 20 | 2 | 4 | 1 | 3 | 3 | 2 | 1 | 2 | 2 | 2 | 2 | 2 | 2 | 2 |
| 21 | 2 | 3 | 4 | 3 | 2 | 1 | 1 | 3 | 3 | 3 | 2 | 2 | 2 | 2 |
| 22 | 4 | 5 | 5 | 5 | 5 | 3 | 2 | 3 | 3 | 3 | 3 | 3 | 3 | 2 |
| 23 | 2 | 3 | 2 | 2 | 1 | 1 | 1 | 3 | 4 | 3 | 3 | 4 | 2 | 2 |
| 24 | 4 | 5 | 5 | 5 | 5 | 5 | 5 | 2 | 3 | 3 | 2 | 2 | 2 | 2 |
| 25 | 2 | 2 | 2 | 3 | 1 | 1 | 1 | 3 | 4 | 4 | 3 | 3 | 2 | 2 |
| 26 | 3 | 4 | 1 | 3 | 3 | 2 | 1 | 3 | 3 | 3 | 3 | 2 | 2 | 2 |
| 27 | 2 | 2 | 1 | 2 | 1 | 3 | 2 | 3 | 4 | 4 | 3 | 3 | 3 | 3 |
| 28 | 4 | 5 | 5 | 5 | 5 | 5 | 5 | 3 | 3 | 3 | 2 | 2 | 2 | 2 |
| 29 | 4 | 5 | 5 | 5 | 4 | 4 | 3 | 3 | 4 | 3 | 3 | 2 | 2 | 2 |
| 30 | 1 | 4 | 2 | 5 | 3 | 2 | 1 | 2 | 2 | 2 | 2 | 2 | 3 | 2 |

Test 2 seven-species greenhouse test

The test was conducted in general like that described in Test 1. In this test, the seeds were planted in flat metal trays, rather than in pots. The compounds were formulated according to the procedure above, except that about 6 g./100 ml. of the compound was dissolved in the surfactant-containing solvent, and about 1 part of the organic solution was diluted with 12 parts of water before application to the trays. The compounds were applied at the rate of 9.0 kg./ha., and the results of

Test 3 multiple-species greenhouse test

In general, the test method was the same as the method of the test above. Various compounds were tested preemergence and postemergence at different application rates which are indicated in the tables below. A number of additional weed and crop species were used in the preemergence tests as is shown in Table 3. Typical postemergence results are shown in Table 4.

Table 3

| Compound of Example No. | Rate of Appln. kg./ha. | Corn | Cotton | Soybean | Wheat | Alfalfa | Sugar Beet | Rice | Cucumber | Tomato | Barnyard Grass | Lambsquarter | large Crabgrass | Mustard | Pigweed | Foxtail | Wildoat | Velvetleaf | Jimson Weed | Morningglory | Zinnia |
|---|---|---|---|---|---|---|---|---|---|---|---|---|---|---|---|---|---|---|---|---|---|
| 1 | 1.1 | 2 | 1 | 2 | 1 | 2 | 4 | 1 | 1 | 2 | 2 | 4 | 4 | 4 | 5 | 2 | 1 | 2 | 2 | 2 | 2 |
| 2 | 4.5 | 2 | 1 | 2 | 3 | 3 | 5 | 2 | 1 | 2 | 2 | 4 | 4 | 4 | 3 | 3 | 1 | 3 | 2 | 3 | 2 |
| 5 | 1.1 | 1 | 1 | 2 | 2 | 2 | 4 | 1 | 2 | 1 | 2 | 4 | 3 | 4 | 3 | 3 | 2 | 3 | 2 | 2 | 1 |
| 6 | 0.28 | 3 | 1 | 1 | 1 | 3 | 3 | 2 | 1 | 2 | 4 | 3 | 5 | 3 | 5 | 4 | 3 | 3 | 3 | 2 | 2 |
| 7 | 1.1 | 3 | 1 | 3 | 2 | 5 | 5 | 2 | 2 | 5 | 3 | 4 | 5 | 3 | 5 | 5 | 3 | 3 | 2 | 2 | 2 |
| 19 | 4.5 | 4 | 2 | 4 | 4 | 5 | 5 | 1 | 2 | 5 | 4 | 5 | 5 | 5 | 5 | 5 | 5 | 4 | 4 | 5 | 5 |
|  | 2.24 | 3 | 1 | 4 | 4 | 5 | 4 | 1 | 1 | 4 | 4 | 5 | 5 | 3 | 5 | 5 | 4 | 3 | 3 | 5 | 3 |
| 20 | 1.1 | 3 | 2 | 3 | 3 | 4 | 5 | 3 | 2 | 2 | 4 | 4 | 5 | 4 | 4 | 5 | 3 | 3 | 3 | 3 | 3 |
|  | 4.5 | 1 | 1 | 1 | 1 | 1 | 2 | 1 | 2 | 3 | 1 | 2 | 1 | 1 | 2 | 2 | 1 | 1 | 2 | 2 | 1 |
|  | 2.24 | 1 | 1 | 1 | 1 | 1 | 1 | 2 | 1 | 1 | 1 | 1 | 1 | 3 | 2 | 3 | 1 | 2 | 3 | 2 | 1 |
| 22 | 1.1 | 4 | 1 | 2 | 2 | 3 | 5 | 2 | 1 | 2 | 3 | 5 | 5 | 3 | 5 | 4 | 2 | 3 | 3 | 2 | 2 |
|  | 0.56 | 2 | 1 | 2 | 2 | 2 | — | 1 | 1 | 1 | 3 | 4 | — | 2 | 5 | 5 | 2 | 3 | 2 | 1 | 1 |
|  | 0.28 | 3 | 1 | 1 | 1 | 1 | — | 2 | 1 | 1 | 2 | 2 | — | 2 | 5 | 3 | 2 | 3 | 2 | 1 | 3 |
| 24 | 4.5 | 3 | 3 | 3 | 2 | 3 | 5 | 2 | 3 | 5 | 4 | 4 | 5 | 5 | 5 | 5 | 4 | 4 | 4 | 3 | 3 |
|  | 2.24 | 2 | 1 | 2 | 1 | 2 | 5 | 1 | 1 | 1 | 5 | 5 | 5 | 5 | 5 | 5 | 2 | 3 | 4 | 4 | 3 |
|  | 1.1 | 1 | 1 | 1 | 2 | 2 | 4 | 2 | 1 | 5 | 3 | 4 | 4 | 4 | 4 | 4 | 2 | 2 | 1 | 2 | 2 |
| 26 | 4.5 | 3 | 1 | 2 | 2 | 5 | 5 | 1 | 3 | 5 | 5 | 5 | 5 | 5 | 4 | 5 | 2 | 3 | 4 | 4 | 3 |
|  | 2.24 | 2 | 1 | 1 | 2 | 2 | 3 | 1 | 2 | 4 | 3 | 4 | 4 | 3 | 5 | 3 | 2 | 2 | 2 | 2 | 2 |
|  | 1.1 | 3 | 1 | 2 | 1 | 2 | 4 | 2 | 2 | 2 | 3 | 5 | 5 | 4 | 5 | 5 | 3 | 3 | 2 | 4 | 3 |
| 28 | 4.5 | 3 | 1 | 3 | 2 | 3 | 4 | 1 | 3 | 3 | 3 | 5 | 5 | 3 | 5 | 5 | 3 | 3 | 2 | 2 | 2 |
|  | 2.24 | 2 | 1 | 2 | 2 | 3 | 4 | 1 | 1 | 2 | 3 | 5 | 5 | 4 | 5 | 4 | 2 | 2 | 2 | 2 | 2 |
|  | 1.1 | 2 | 1 | 2 | 2 | 2 | 4 | 1 | 2 | 3 | 3 | 4 | 5 | 4 | 5 | 5 | 2 | 3 | 2 | 3 | 2 |
| 29 | 4.5 | 2 | 1 | 2 | 2 | 2 | 3 | 1 | 2 | 2 | 2 | 5 | 5 | 3 | 5 | 4 | 2 | 2 | 2 | 3 | 2 |
|  | 2.24 | 2 | 1 | 1 | 1 | 2 | 3 | 2 | 1 | 2 | 2 | 4 | 5 | 3 | 4 | 3 | 2 | 2 | 2 | 2 | 2 |
|  | 1.1 | 1 | 1 | 1 | 1 | 1 | 2 | 1 | 1 | 1 | 1 | 3 | 3 | 3 | 4 | 3 | 2 | 1 | 1 | 2 | 1 |
| 30 | 4.5 | 1 | 1 | 1 | 1 | 1 | 2 | 2 | 1 | 2 | 2 | 2 | 2 | — | 2 | 2 | 1 | 3 | 1 | 1 | 1 |
|  | 2.24 | — | 1 | 1 | 1 | 1 | 2 | 1 | 1 | 2 | 1 | 2 | 2 | — | 1 | 1 | — | 1 | — | — | 1 |
|  | 1.1 | — | 1 | 1 | 1 | 1 | 2 | 1 | 1 | 1 | 1 | 3 | 3 | — | 1 | 1 | 1 | 1 | — | 1 | 1 |

Table 4

| Compound of Example No. | Rate of Appln. kg./ha. | Postemergence | | | | | | |
|---|---|---|---|---|---|---|---|---|
| | | Corn | Large Crabgrass | Pigweed | Foxtail | Velvetleaf | Morningglory | Zinnia |
| 23 | 4.5 | 3 | 2 | 3 | 3 | 3 | 3 | 2 |
|    | 2.24 | 2 | 2 | 2 | 2 | 2 | 3 | 2 |
|    | 1.1 | 2 | 2 | 3 | 2 | 2 | 3 | 2 |
| 25 | 4.5 | 4 | 3 | 3 | 3 | 3 | 3 | 3 |
|    | 2.24 | 3 | 3 | 3 | 3 | 3 | 3 | 3 |
|    | 1.1 | 3 | 3 | 3 | 3 | 2 | 3 | 3 |
| 27 | 4.5 | 4 | 4 | 4 | 3 | 3 | 3 | 3 |
|    | 2.24 | 4 | 3 | 3 | 3 | 3 | 3 | 3 |
|    | 1.1 | 4 | 4 | 3 | 2 | 3 | 3 | 3 |

The broad-spectrum activity of the compounds of this invention is clearly illustrated by the above examples. The test results point up the efficacy of the compounds against annual grasses and broadleaf weeds. Plant scientists will recognize that the exemplified activity of the compounds shows that the compounds are broadly effective against herbaceous weeds.

As the above test results demonstrate, an important embodiment of this invention is a method of reducing the vigor of unwanted herbaceous plants which comprises contacting the plants with a herbicidally-effective amount of one of the compounds described above. In the context of this invention, the term "reducing the vigor of" is used to refer to the effects of the compounds both in killing unwanted herbaceous plants, and in injuring, stunting, dwarfing, and otherwise preventing the normal growth and development of such plants. The term "herbicidally-effective amount" refers to an amount of a compound of this invention which is sufficient to bring about such effects on unwanted herbaceous plants.

In some instances, as is clear from the test results, the whole population of the contacted plant is killed. In other instances, some of the plants are killed and some of them are injured, and in still other instances, none of the plants are killed but are merely injured by application of the compound. It will be understood that reducing the vigor of the unwanted plant population by injuring the individual plants, or by killing some and injuring some, is beneficial even though some part of the plant population survives application of the compound. The plants, the vigor of which has been reduced, are unusually susceptible to the stresses, such as disease, drought, lack of nutrients and so forth, which normally afflict plants.

Thus, the treated plants, even though they survive application of the compound, are likely to expire due to stress of the environment. Further, if the treated plants are growing in cropland, the crop, growing normally, tends to shade out the treated plants of reduced vigor. The crop, therefore, has a great advantage over the treated unwanted plants in the competition for nutrients and sunlight. Still further, when the treated plants are growing in fallow land, or industrial property which is desired to be bare, the fact that their vigor is reduced necessarily tends to minimize the treated plants' consumption of water and nutrients, and also minimizes the fire hazard and nuisance which the plants present.

The compounds are herbicidally effective when applied both preemergence and postemergence. Thus, they can be applied to the soil to kill and injure weeds by soil contact when the weed seeds are germinating and emerging, and can also be used to kill and injure growing weeds by direct contact with the exposed portions of the weeds. Preemergence application of the compounds, wherein the unwanted herbaceous plants are contacted with the compound through application to the soil before emergence of the plants, is preferred. Seeds of unwanted plants, which are contacted with the compounds by soil application, are here regarded as plants.

Preemergence applications of the compounds are effective, as the examples show, whether the compounds are applied to the surface of the soil or are incorporated in the soil.

The preferred compounds of this invention, which are also the compounds with which the herbicidal method is preferably carried out, and with which the herbicidal compositions are preferably prepared, are 4-methoxy-1-methyl-3-phenyl-5-(3-trifluoromethylphenyl)pyridinium trifluoromethanesulfonate, 4-chloro-3-(4-chlorophenyl)-1-methyl-5-(3-trifluoromethylphenyl)pyridinium iodide, 4-chloro-1-methyl-3-phenyl-5-(3-trifluoromethylphenyl)pyridinium iodide, 4-chloro-3,5-bis(3-chlorophenyl)-1-methylpyridinium iodide and 4-bromo-3-(3-chlorophenyl)-5-(4-chlorophenyl)-1-methylpyridinium iodide.

As the examples above illustrate, the compounds are acceptably safe to a number of crops, such as cotton, cucumber, wheat and rice when applied at proper rates and at appropriate times.

The best application rate of a given compound of the invention for the control of a given plant varies, of course, depending upon the method of compound application, climate, soil texture, water and organic matter contents of the soil and other factors known to those skilled in plant science. It will be found, however, that the optimum application rate is in the range of from about 0.25 to about 20 kg./ha. in virtually every case. The optimum rates will usually be found to be within the preferred range of from about 1 to about 10 kg./ha.

The time when the compounds should be applied to the soil or the unwanted plants is widely variable, since the compounds are effective both preemergence and postemergence. At least some control will result from application of the compounds at any time when plants are growing or germinating. They may also be applied to the soil during a dormant season to kill weeds germinating during the following warm season.

When the compounds are used for weed control in an annual crop, it is usually best to apply a preemergence application of the compound to the soil at the time the crop is being planted. If the compound is to be soil incorporated, it will usually be applied and incorporated immediately before planting. If it is to be surface applied, it is usually simplest to apply the compound immediately after planting.

The compounds are applied to the soil or to emerged plants in the manners usual in agriculture. They may be applied to the soil in the form of either water-dispersed or granular formulations, the preparation of which will be discussed below. Usually, water-dispersed formulations will be used for the application of the compounds to emerged weeds. The formulations are applied with any of the many types of sprayers and granular applicators which are in wide use for the distribution of agricultural chemicals over soil or standing vegetation. When a compound is to be soil-incorporated, any of the usual soil incorporation equipment, such as the disc harrow, the power-driven rotary hoe and the like, are effective.

The compounds are useful for the control of aquatic weeds, as well as terrestrial undesired plants. Such aquatic weeds as duckweed, water milfoil, hydrilla and the like are controlled when the compounds are dispersed in the infested water at concentrations in the range of from about 0.1 to about 10 p.p.m. by weight. The compounds are applied to water in the form of the same types of herbicidal compositions used for other herbicidal uses.

The compounds are normally used in the practice of the method of this invention in the form of the herbicidal compositions which are an important embodiment of the invention. An herbicidal composition of this invention comprises a compound useful in the method of the invention and an inert carrier. In general, the compositions are formulated in the manners usual in agricultural chemistry, and are novel only because of the vital presence of the herbicidal compound.

Very often, the compounds are formulated as concentrated compositions which are applied either to the soil or the foliage in the form of water dispersions or emulsions containing in the range of from about 0.1 percent to about 5 percent of the compound. Water-dispersible or emulsifiable compositions are either solids usually known as wettable powders, or liquids usually known as emulsifiable concentrates. Wettable powders comprise an intimate, finely-divided mixture of the compound, an inert carrier and surfactants. The concentration of the compound is usually from about 10 percent to about 90 percent. The inert carrier is usually chosen from among the attapulgite clays, the kaolin clays, the montmorillonite clays, the diatomaceous earths or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates and nonionic surfactants such as ethylene oxide adducts of phenol.

Typical emulsifiable concentrates of the compounds comprise a convenient concentration of the compound, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a compound is to be applied to the soil, as for a preemergence application of the compound, it is convenient to use a granular formulation. Such a formulation typically comprises the compound dispersed on a granular inert carrier such as coarsely ground clay. The particle size of granules usually ranges from about 0.1 to about 3 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product.

It has become customary in agricultural chemistry to apply two or even more agricultural chemicals simultaneously in order to control weeds of many different types, or weeds and other pests, with a single application of chemicals. The compounds of this invention lend themselves well to combination with other agricultural chemicals and may usefully be combined with insecticides, fungicides, nematicides and other herbicides as may be desirable and convenient.

We claim:

1. A compound of the formula

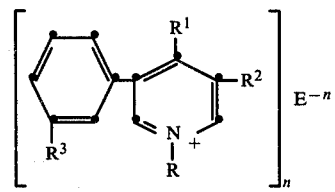

wherein R represents methyl or ethyl;
$R^1$ represents halo, methoxy, or dimethylamino;
$R^2$ represents hydrogen, phenoxy, $C_1$-$C_4$ alkyl, $C_1$-$C_4$ alkoxy, phenyl or phenyl monosubstituted with chloro, bromo, fluoro, trifluoromethyl, $C_1$-$C_3$ alkyl or $C_1$-$C_3$ alkoxy;
$R_3$ represents $C_1$-$C_3$ alkyl, $C_1$-$C_3$ alkoxy, trifluoromethyl, chloro, fluoro or bromo;
E represents an anion capable of forming a pyridinium salt; and
n represents an integer of 1 to 3.

2. A compound of claim 1 wherein $R^1$ represents halo or methoxy.

3. A compound of claim 2 wherein $R^2$ represents alkyl, phenyl or phenyl monosubstituted with chloro, bromo, fluoro, trifluoromethyl, methyl or methoxy.

4. A compound of claim 3 wherein $R^3$ represents methyl, methoxy, trifluoromethyl, chloro, fluoro or bromo.

5. A compound of claim 4 wherein E represents halide, trifluoromethanesulfonate, fluorosulfonate, methanesulfonate or toluenesulfonate.

6. The compound of claim 5 which is 4-methoxy-1-methyl-3-phenyl-5-(3-trifluoromethylphenyl)-pyridinium trifluoromethanesulfonate.

7. The compound of claim 5 which is 4-chloro-3-(4-chlorophenyl)-1-methyl-5-(3-trifluoromethylphenyl)-pyridinium iodide.

8. The compound of claim 5 which is 4-chloro-1-methyl-3-phenyl-5-(3-trifluoromethylphenyl)-pyridinium iodide.

9. The compound of claim 5 which is 4-chloro-3,5-bis(3-chlorophenyl)-1-methylpyridinium iodide.

10. The compound of claim 5 which is 4-bromo-3-(3-chlorophenyl)-5-(4-chlorophenyl)-1-methylpyridinium iodide.

11. A herbicidal composition comprising an agriculturally-acceptable carrier and a herbicidally-effective amount of a compound of claim 1.

12. A composition of claim 11 wherein $R^1$ represents halo or methoxy.

13. A composition of claim 12 wherein $R^2$ represents alkyl, phenyl or phenyl monosubstituted with chloro, bromo, fluoro, trifluoromethyl, methyl or methoxy.

14. A composition of claim 13 wherein $R^3$ represents methyl, methoxy, trifluoromethyl, chloro, fluoro or bromo.

15. A composition of claim 14 wherein E represents halide, trifluoromethanesulfonate, fluorosulfonate, methanesulfonate or toluenesulfonate.

16. A composition of claim 15 in which the compound is 4-methoxy-1-methyl-3-phenyl-5-(3-trifluoromethylphenyl)pyridinium trifluoromethanesulfonate.

17. A composition of claim 15 in which the compound is 4-chloro-3-(4-chlorophenyl)-1-methyl-5-(3-trifluoromethylphenyl)pyridinium iodide.

18. A composition of claim 15 in which the compound is 4-chloro-1-methyl-3-phenyl-5-(3-trifluoromethylphenyl)pyridinium iodide.

19. A composition of claim 15 in which the compound is 4-chloro-3,5-bis(3-chlorophenyl)-1-methylpyridinium iodide.

20. A composition of claim 15 in which the compound is 4-bromo-3-(3-chlorophenyl)-5-(4-chlorophenyl)-1-methylpyridinium iodide.

21. A method of reducing the vigor of unwanted herbaceous plants which comprises contacting the plants with a herbicidally-effective amount of a compound of claim 1.

22. A method of claim 21 wherein the amount of the compound is from about 0.25 to about 20 kg./ha.

23. A method of claim 22 wherein the amount of the compound is from about 1 to about 10 kg./ha.

24. A method of claim 21 wherein $R^1$ represents halo or methoxy.

25. A method of claim 24 wherein $R^2$ represents alkyl, phenyl or phenyl monosubstituted with chloro, bromo, fluoro, trifluoromethyl, methyl or methoxy.

26. A method of claim 25 wherein $R^3$ represents methyl, methoxy, trifluoromethyl, chloro, fluoro or bromo.

27. A method of claim 26 wherein E represents halide, trifluoromethanesulfonate, fluorosulfonate, methanesulfonate or toluenesulfonate.

28. The method of claim 27 in which the compound is 4-methoxy-1-methyl-3-phenyl-5-(3-trifluoromethylphenyl)-pyridinium trifluoromethanesulfonate.

29. The method of claim 27 in which the compound is 4-chloro-3-(4-chlorophenyl)1-methyl-5-(3-trifluoromethylphenyl)pyridinium iodide.

30. The method of claim 27 in which the compound is 4-chloro-1-methyl-3-phenyl-5-(3trifluoromethylphenyl)-pyridinium iodide.

31. The method of claim 27 in which the compound is 4-chloro-3,5-bis(3-chlorophenyl)-1-methylpyridinium iodide.

32. The method of claim 27 in which the compound is 4-bromo-3-(3-chlorophenyl)-5-(4-chlorophenyl)-1-methylpyridinium iodide.

* * * * *